(12) United States Patent
Sukuru

(10) Patent No.: US 8,293,270 B2
(45) Date of Patent: Oct. 23, 2012

(54) LIPOPHILIC VEHICLE-BASED DUAL CONTROLLED RELEASE MATRIX SYSTEM

(75) Inventor: Karunakar Sukuru, High Point, NC (US)

(73) Assignee: Banner Pharmacaps, Inc., High Point, NC (US)

( * ) Notice: Subject to any disclaimer, the term of this patent is extended or adjusted under 35 U.S.C. 154(b) by 530 days.

(21) Appl. No.: 11/553,349

(22) Filed: Oct. 26, 2006

(65) Prior Publication Data

US 2007/0092560 A1    Apr. 26, 2007

Related U.S. Application Data

(60) Provisional application No. 60/730,514, filed on Oct. 26, 2005.

(51) Int. Cl.
*A61K 9/66* (2006.01)
(52) U.S. Cl. .......................................................... 424/452
(58) Field of Classification Search .................. None
See application file for complete search history.

(56) References Cited

U.S. PATENT DOCUMENTS

| | | | | |
|---|---|---|---|---|
| 4,424,235 A | * | 1/1984 | Sheth et al. ................... | 514/567 |
| 5,447,729 A | | 9/1995 | Belenduik et al. | |
| 5,498,422 A | * | 3/1996 | Nakamichi et al. ........... | 424/451 |
| 5,609,882 A | | 3/1997 | Aoki et al. | |
| 5,662,933 A | * | 9/1997 | Baichwal et al. ............. | 424/457 |
| 6,027,746 A | | 2/2000 | Lech | |
| 6,056,977 A | * | 5/2000 | Bhagwat et al. ............. | 424/488 |
| 6,251,426 B1 | | 6/2001 | Gullapalli | |
| 2001/0004459 A1 | | 6/2001 | Barthelemy et al. | |
| 2002/0160041 A1 | | 10/2002 | Gutierrez-Rocca | |
| 2003/0091603 A1 | | 5/2003 | Ohmori et al. | |
| 2003/0203030 A1 | | 10/2003 | Ashton et al. | |
| 2004/0033257 A1 | | 2/2004 | Iyer et al. | |
| 2004/0052731 A1 | | 3/2004 | Hirsh et al. | |
| 2005/0152968 A1 | | 7/2005 | Brophy et al. | |
| 2005/0244489 A1 | * | 11/2005 | Paris ............................ | 424/451 |
| 2005/0255152 A1 | * | 11/2005 | Edwards et al. .............. | 424/450 |
| 2006/0286172 A1 | | 12/2006 | Mahashabde | |

FOREIGN PATENT DOCUMENTS

| | | | |
|---|---|---|---|
| AU | 199719991 | | 11/1997 |
| GB | 2283171 A | * | 6/1994 |
| GB | 2283172 | | 5/1995 |
| GB | 2283172 A | * | 5/1995 |
| GB | 2331458 | | 5/1999 |
| WO | WO 99/36060 | | 7/1999 |
| WO | WO 01/22942 | | 4/2001 |
| WO | WO02/11701 | | 2/2002 |
| WO | WO 01/034119 | | 9/2002 |
| WO | WO 02/083177 | | 10/2002 |
| WO | WO 03/086392 | | 10/2003 |
| WO | WO-03086368 A | * | 10/2003 |
| WO | WO 2004/030658 | | 4/2004 |
| WO | WO 2005/009409 | | 2/2005 |
| WO | WO 2005/009409 A2 | * | 2/2005 |
| WO | WO 2005/041929 | | 5/2005 |

OTHER PUBLICATIONS

Karabulut et al. (Food Chemistry 2003, 81, 453-456).*
Definition: colloid. From: Lewis Ed. Hawley's Concensed Chemical Dictionary. John Wiley & Sons, Inc.: NY 1997.*
Al-Gohary and Hosny, "Effect of antacid magaldrate oral suspension on in-vitro and in-vivo availability of indomethacin in dogs", *Pharmareatica Acta Helvetiate,*, 72:81436, (1997).
PubMed Health, "Misoprostol", U.S. Natl. library of Medcine, NIH (2008).

\* cited by examiner

*Primary Examiner* — Mina Haghighatian
*Assistant Examiner* — Jessica Kassa
(74) *Attorney, Agent, or Firm* — Pabst Patent Group LLP

(57) ABSTRACT

A lipophilic vehicle-based dual controlled-release matrix, suitable for encapsulation in hard or soft capsules, has been developed. The matrix is in the form of a suspension, which allows for easier formulation of low dose compounds and/or compounds which are moisture sensitive. The matrix includes two rate controlling barriers for the controlled release of one or more pharmaceutically active agents. The primary rate controlling barrier includes a relatively lipophilic oily vehicle. The primary rate controlling barrier may further comprise or more excipients, dissolved in the lipophilic vehicle, which themselves have rate controlling properties. The secondary rate controlling barrier is a hydrogel-forming polymeric material which is dispersed in the primary rate controlling barrier. As the primary rate controlling barrier breaks down, the pharmaceutically active agent is slowly released and the surrounding aqueous media begins to percolate into the polymer matrix. This results in hydration of the polymer and subsequent formation of a hydrogel, which controls the release of the drug by diffusion through, and/or erosion of, the hydrogel. By dispersing or suspending part of the pharmaceutically active agent in the primary rate controlling vehicle, a dual release profile can be obtained. The combination of release of the drug from the lipophilic oily vehicle and release of the drug from the hydrogel allows for the modulation of drug release for up to 24 hours. This system is particularly useful for moisture sensitive drugs as the oily layer prevents water migration from the shell in to the fill.

19 Claims, 3 Drawing Sheets

LIPOPHILIC VEHICLE-BASED DUAL CONTROLLED RELEASE MATRIX SYSTEM

CROSS-REFERENCE TO RELATED APPLICATION

Priority is claimed to U.S. Application No. 60/730,514, filed Oct. 26, 2005.

FIELD OF THE INVENTION

The present invention is generally in the field of pharmaceutical compositions, specifically controlled release pharmaceutical compositions.

BACKGROUND OF THE INVENTION

Controlled release (CR) formulations are useful in situations where drug release over an extended period of time is required, such as repetitive, intermittent dosings of a drug from one or more immediate release systems. Controlled release drug delivery systems are used to improve the therapeutic response by providing blood levels that are more consistent and stable compared to immediate release dosage forms. Existing CR dosage forms are typically based on matrix tablets or coated tablets or capsules filled with coated drug particles or granules. These systems have several drawbacks, however including the lack of content uniformity and homogeneity, particularly with compounds present in low dosages. Moreover, compounds which are used in low dosages, as well as compounds which are moisture sensitive, can be difficult to handle in solid form, which is the form typically used to prepare tablets or powder-filled hard gelatin capsules.

U.S. Patent Application Publication No. 2004/0052731 to Hirsh et al. describes abuse deterrent pharmaceutical compositions. The compositions contain a drug which has been modified to increase its lipophilicity. The modified drug is dispersed within microparticles composed of a material that is either slowly soluble or not soluble in water. The drug containing microparticles or drug particles can be coated with one or more coating layers, where at least one coating is water insoluble and preferably organic solvent insoluble, but enzymatically degradable by enzymes in the GI tract.

Controlled release formulations, particularly of drugs which are prone to abuse such as opioid analgesics, can be susceptible to misuse. Currently available sustained release formulations of such drugs, which contain a relatively large amount of drug meant to be released from the formulation over an extended period of time, are particularly attractive to abusers since the sustained release action can be destroyed by crushing or grinding the formulation. The resulting material (i.e., the crushed formulation) can no longer control the release of drug. Depending on the drug, abusers can then snort the material, swallow the material or dissolve the material in water and subsequently inject it intravenously. The dose of drug contained in the formulation is thus absorbed immediately through the nasal or GI mucosa (for snorting or swallowing, respectively) or is administered in a bolus to the systemic circulation (for IV injection). These methods result in the rapid bioavailability of relatively high doses of drug, giving the abuser a "high". Since relatively simple methods (crushing, grinding, chewing and/or dissolution in water) can be used to transform such formulations into an abusable form, they provide virtually no deterrent to a potential abuser.

There is a need for a liquid controlled-release composition in which low dose compounds and compounds which are moisture sensitive can be more easily formulated.

There also exists a need for a controlled release formulation which can minimize or prevent the misuse of drugs which are prone to abuse by making it more difficult for the drug to be extracted from the dosage form.

Therefore, it is an object of the present invention to provide a dual controlled release matrix for the formulation of low dose and/or moisture sensitive drugs, and methods of manufacture thereof.

It is further an object of the invention to provide a dual controlled release matrix which can minimize or prevent the misuse of drugs which are prone to abuse.

BRIEF SUMMARY OF THE INVENTION

A lipophilic vehicle-based dual controlled-release liquid matrix, suitable for encapsulation in hard or soft capsules, has been developed. The matrix is in the form of a suspension, which allows for easier formulation of low dose compounds and/or compounds which are moisture sensitive. The matrix includes two rate controlling barriers for the controlled release of one or more pharmaceutically active agents. The primary rate controlling barrier includes a relatively lipophilic oily vehicle. The primary rate controlling barrier may further include one or more excipients, dissolved in the lipophilic vehicle, which themselves have rate controlling properties. The secondary rate controlling barrier is a hydrogel-forming polymeric material which is dispersed in the primary rate controlling barrier. As the primary rate controlling barrier degrades, the pharmaceutically active agent is slowly released and the surrounding aqueous media begins to percolate into the polymer matrix. This results in hydration of the polymer and formation of a hydrogel, which controls the release of the drug by diffusion through, and/or erosion of, the hydrogel. By dispersing or suspending part of the pharmaceutically active agent in the primary rate controlling vehicle, a dual release profile can be obtained. The combination of release of the drug from the lipophilic oily vehicle and release of the drug from the hydrogel allows for the modulation of drug release for up to 24 hours. This system is particularly useful for moisture sensitive drugs as the oily layer prevents water migration from the shell into the fill.

The presence of the hydrogel-forming polymeric material, which forms a hydrogel upon contact with aqueous media, thereby trapping the drug, makes extraction of the drug from the dosage form more difficult. This feature should be beneficial in preventing or minimizing the misuse of dosage forms which contain drugs which are prone to abuse.

DETAILED DESCRIPTION OF THE INVENTION

Figure 1:
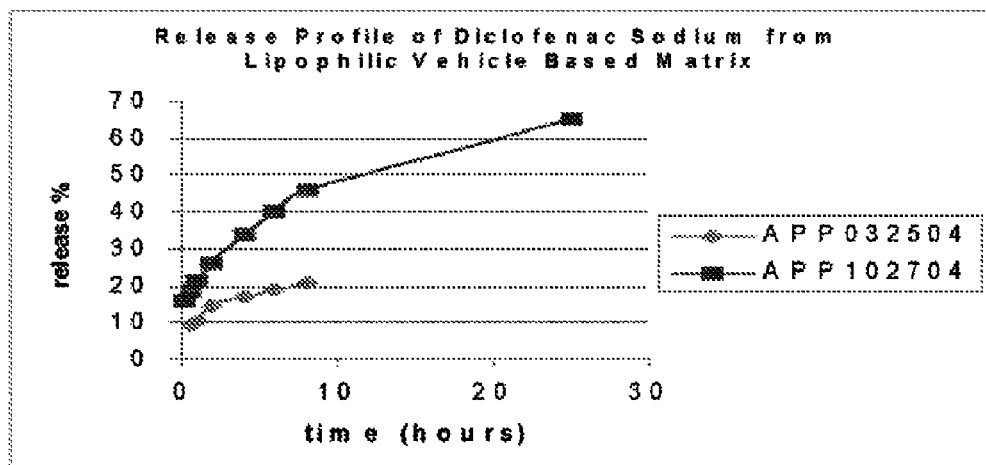
FIG. 1 shows the release profile of Diclofenac sodium (% Diclofenac sodium) versus time (hours) from a lipophilic vehicle-based matrix.

Liquid controlled release matrix systems suitable for encapsulation in a soft gelatin capsule, a non-animal soft gelatin capsule, or a liquid filled hard shell gelatin capsule have been developed. The matrix includes a hydrogel-forming polymeric material dispersed in a lipophilic oily vehicle. The use of a liquid matrix minimizes the problems associated with handling powders, namely content uniformity and homogeneity as well as eliminates the need for organic solvents which are often required in the manufacture of tablets or powder-filled hard shell capsules.

I. Controlled Release Matrix

Definitions

As used herein, a "dual controlled-release matrix" refers to a matrix containing a primary rate controlling barrier and a secondary rate controlling barrier dispersed in the primary rate controlling barrier. The primary rate controlling barrier includes a lipophilic oily vehicle. The secondary rate controlling barrier includes a hydrogel-forming polymeric material. Drug is released from the primary rate controlling barrier as the barrier degrades over time. Degradation of the primary rate controlling barrier allows water to contact the secondary rate controlling barrier resulting in formation of a hydrogel. Drug molecules trapped within the hydrogel are released over time by diffusion through and/or erosion of the hydrogel.

As used herein, "hydrogel" refers to materials which swell extensively in water and dissolve or erode with time depending on the viscosity and the molecular weight of the material.

As used herein, "lipophilic oily vehicle", "lipophilic vehicle" or "lipophilic base" refers to one or more compounds which are electrically neutral and non-polar. Lipophilic compounds are soluble or partially soluble in fats, oils, or lipids.

As used herein, a "biphasic release profile" refers to a drug release profile having two distinct phases or stages.

As used herein, "controlled release" refers to a release profile of a drug for which the drug release characteristics of time course and/or location are chosen to accomplish therapeutic or convenience objectives not offered by conventional dosage forms such as solutions, or promptly dissolving dosage forms. Delayed release, extended release, and pulsatile release and their combinations are types of controlled release.

A. Lipophilic Oily Vehicle

The hydrogel-forming polymeric material is dispersed in a lipophilic oily vehicle. Exemplary lipophilic oily vehicles include, but are not limited to, vegetable oils, medium chain mono-, di-, and triglycerides, glyceryl stearates (available from Sasol under the tradename IMWITOR®), polyoxyethylated oleic glycerides (available from Gattefosse, S.A., Saint Priest, France, under the tradename LABRAFIL®), mineral oil, mono- and diglyceride emulsifiers such as glyceryl monooleate, glyceryl monocaprate, glyceryl monocaprylate, propylene glycol monocaprylate, and propylene glycol monolaurate (available from Abitec Corp., Columbus, Ohio, under the tradename CAPMUL®), and dimethylpolysiloxanes such as simethicone. The lipophilic oily vehicle is present in an amount from about 3% to about 80% by weight, more preferably from about 15% to about 75%, by weight of the matrix. Incorporation of the drug into a lipophilic vehicle reduces the aqueous extractability of the drug.

B. Hydrogel-Forming Polymers

Exemplary hydrogel-forming polymer materials include cellulose ethers preferably different viscosity/molecular weight grades of hypromelloses such as hydroxypropyl methyl cellulose (HPMC K4M to K100M available from Dow Chemical); cross-linked acrylates such as CARBOPOL®; alginates; guar or xanthan gum; carrageenan; carboxymethylcellulose; and mixtures thereof. The hydrogel-forming polymeric material is present in an amount from about 2% to about 80% by weight, preferably 3% to 50% by weight of the matrix.

Incorporation of the drug into the hydrogel-forming polymeric material can protect the drug from exposure upon mechanical disruption, such as grinding, chewing or cutting and thus prevent or minimize misuse. Further, hydrogel-forming polymeric materials tend to be hydrophilic and thus resist extraction of the trapped drug by organic solvents.

C. Rate Controlling Excipients

The lipophilic vehicle can be combined with one or more rate controlling excipients including, but not limited to, glyceryl behenate, gelucire, cremophor, hydrogenated vegetable oil, bees wax, cellulosic polymers such as hypromellose, alginates, CARBOPOL® and combinations thereof. A rate controlling excipient is defined as a compound which possesses rate controlling properties. The one or more excipients are present in an amount from about 0% to about 50%, more preferably from about 2% to about 30% by weight of the matrix.

The lipophilic vehicle can further include one or more surfactants. Suitable surfactants include, but are not limited to, polysorbates (available from ICI under the tradename TWEEN®), sorbitan monoesters (available from ICI under the tradename SPAN®), caprylocaproyl macrogol-8 (available from Gattefosse S.A., Saint Priest, France under the tradename Labrasol®), cremophores, glyceryl monooleate/stearate and mixtures thereof. The surfactants are present in an amount from about 1% to about 30% by weight of the matrix, preferably from about 3% to about 10% by weight of the matrix. By using the appropriate excipients, a biphasic release profile, with an initial rapid release of drug followed by a sustained slow release of drug, can be obtained. For example, FIG. 1 shows the release profile of Diclofenac sodium from a lipophilic vehicle-based dual controlled-release matrix. The system exhibits a release profile wherein approximately 45% of the diclofenac sodium has been released after 10 hours and approximately 65% of the diclofenac sodium has been released after about 25 hours.

D). Therapeutic, Prophylactic and Diagnostic Agents

Therapeutic, prophylactic or diagnostic agents can be encapsulated. Exemplary drug agents include, but are not limited to, analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; anti-infective agents; anti-inflammatory agents; antimigraine agents; antineoplastic agents; antiparkinson drugs; antipruritic agents; antipsychotic agents; antipyretic agents; antispasmodic agents; antitubercular agents; antiulcer agents; antiviral agents; anxiolytic agents; appetite suppressants (anorexic agents); attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; sialagogues, steroids; smoking cessation agents; sympathomimetics; tranquilizer; vasodilators; beta-agonist; tocolytic agents, and combinations thereof.

The agents can be administered as the neutral acid or base or as pharmaceutically acceptable salt. As used herein, "pharmaceutically acceptable salt" refer to derivatives of the disclosed compounds wherein the parent compound is modified by making the acid- or base-addition salts thereof. Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric acid; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704, the disclosure of which is hereby incorporated by reference.

E. Excipients and Additives

These formulations may include other standard pharmaceutical excipients, including plasticizers, crystallization inhibitors, wetting agents, bulk filling agents, solubilizers, bioavailability enhancers, solvents, pH-adjusting agents and combinations thereof.

II. Capsule Shell Composition

A. Gelatin Capsules

Gelatin is the product of the partial hydrolysis of collagen. Gelatin is classified as either Type A or Type B gelatin. Type A gelatin is derived from the acid hydrolysis of collagen while Type B gelatin is derived from the alkaline hydrolysis of collagen. Traditionally, bovine bones and skins have been used as raw materials for manufacturing Type A and Type B gelatin while porcine skins have been used extensively for manufacturing Type A gelatin. In general acid-processed gelatins form stronger gels than lime-processed gelatins of the same average molecular weight. The capsules can be formulated as hard or soft gelatin capsules.

B. Non-gelatin Capsules

Non Gelatin Shell-Carrageenan

Carrageenan is a natural polysaccharide hydrocolloid, which is derived from sea weed. It includes a linear carbohydrate polymer of repeating galactose units, without significant a degree of substitution or branching. Most, if not all, of the galactose units on a carrageenan molecule possess a sulfate ester group. There are three main types of carrageenan: cappa, iota and lambda; although minor forms called mu ad nu carrageenan also exist.

C. Other Shell Additives

Other suitable shell additives include plasticizers, opacifiers, colorants, humectants, preservatives, flavorings, and buffering salts and acids.

Plasticizers are chemical agents added to gelatin to make the material softer and more flexible. Suitable plasticizers include glycerin, sorbitol solutions which are mixtures of sorbitol and sorbitan, and other polyhydric alcohols such as propylene glycol and maltitol or combinations thereof.

Opacifiers are used to opacify the capsule shell when the encapsulated active agents are light sensitive. Suitable opacifiers include titanium dioxide, zinc oxide, calcium carbonate and combinations thereof.

Colorants can be used to for marketing and product identification/differentiation purposes. Suitable colorants include synthetic and natural dyes and combinations thereof.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl (collectively known as "parabens") or combinations thereof.

Flavorings can be used to mask unpleasant odors and tastes of fill formulations. Suitable flavorings include synthetic and natural flavorings. The use of flavorings can be problematic due to the presence of aldehydes which can cross-link gelatin. As a result, buffering salts and acids can be used in conjunction with flavorings that contain aldehydes in order to inhibit cross-linking of the gelatin.

D. Enteric Coatings or Shell Additives

The capsules can be encapsulated in, or include within the shell, enteric coatings. In a preferred embodiment using an enteric polymer, the capsule shell is prepared from a mass comprising a film-forming polymer, an acid insoluble polymer, an aqueous solvent, and optionally a plasticizer. Suitable film-forming polymers include gelatin. Suitable acid-insoluble polymers include acrylic-acid/methacrylic acid copolymers. The acid-insoluble polymer is present in an amount from about 8% to about 20% by weight of the wet gel mass. The weight ratio of acid-insoluble polymer to film-forming polymer is from about 25% to about 50%. The aqueous solvent is water or an aqueous solution of alkalis such as ammonia or diethylene amine or hydroalcoholic solutions of the same. Suitable plasticizers include glycerin and triethylcitrate. Enteric capsule shells and a method of making the capsule shell are described in WO 2004/030658 to Banner Pharmacaps, Inc.

III. Methods of Making

The dual controlled release matrix can be prepared using a lipophilic vehicle that is a solid or a liquid at room temperature. If the lipophilic vehicle is a solid at room temperature, it can be prepared by melting the lipophilic vehicle to form a liquid base. Optionally, one or more rate controlling excipients, such as glyceryl behanate, polyglycolized glyceride (gelucire), bees wax, hydrogenated vegetable oil or vegetable shortening, are solubilized or dissolved in the lipophilic oily vehicle. Additional liquid excipients, such as surfactants, can also be dispersed in the lipophilic vehicle. Generally, the active agent is first added to a hydrogel-forming polymeric material to form a secondary rate controlling barrier, and then the secondary rate controlling barrier is dispersed in the lipophilic vehicle. The secondary rate controlling barrier is dispersed in the lipophilic oily vehicle by mixing or homogenizing the hydrogel-forming polymeric material with the lipophilic base at a temperature above the congealing temperature of the lipophilic base. In some embodiments, the active agent is dispersed in the lipophilic vehicle separately from the hydrogel-forming polymeric material. The active agent is dispersed in the lipophilic vehicle by mixing or homogenization. The fill material, which includes the lipophilic oily vehicle, the hydrogel-forming polymeric material and the active agent, is then dearated to remove any trapped air, such as by applying a vacuum.

B. Encapsulation of the Dual Controlled-Release Matrix

The deaerated fill material described above can be encapsulated at room temperature or at elevated temperatures (up to 35° C. for soft gelatin capsules and up to 60° C. for non-animal soft shell capsules) to facilitate the fill flow. Encapsulation in soft shell capsules is done using a rotary die encapsulation machine using standard procedures. The capsules are dried to the desired hardness and/or moisture content to facilitate the handling of the capsules during packaging, shipping, and storage.

Any agent which requires controlled release can be encapsulated in the lipophilic-based vehicle matrix with a fill weight range of 100 mg to 2200 mg in a capsule suitably sized for swallowing. The capsules will be processed following standard procedures and can be packaged in either bottles or blisters packs.

EXAMPLES

Example 1

Preparation of a Diclofenac Fill Formulation

A lipophilic vehicle-based dual controlled-release matrix system was prepared containing the following ingredients.

| Name of the ingredient | % wt. |
| --- | --- |
| MCT | 68.5 |
| Glyceryl behanate | 2.5 |
| HPMC K4M | 2.5 |
| HPMC K15M | 1.25 |
| Aerosil 200 | 0.25 |
| Diclofenac sodium | 25 |

Glyceryl behanate was dissolved in medium chain triglycerides ("MCT") at about 70° C. Aerosil 200, HPMC K4M and HPMC K15M, in that order, were dispersed in the glyceryl behanate/MCT mixture with continuous mixing, just above the congealing temperature of the glyceryl behanate/MCT mixture. Suitable mixer include a propeller blade or saw toothed blade mixer or a homogenizer. Diclofenac sodium was dispersed in the above mixture and mixed until a homogeneous mass was obtained. The mass was deaerated to remove any trapped air by applying a vacuum. The mass was then encapsulated in a soft shell capsule or a liquid filled hard shell capsule. The above procedure was used to prepare the diltiazem hydrochloride and ibuprofen fill formulations.

In vitro drug release studies were conducted using a USP dissolution apparatus II (paddles) at 50 rpm. The results are shown in FIG. 1. Experiments were conducted in dissolution media at a temperature of 37.0±0.5° C., for 24 hours in 6.8 phosphate buffer. Samples were periodically withdrawn and analyzed for Diclofenac sodium content using the ultraviolet ("UV") method. The samples were analyzed at a wavelength of 276 nm.

Example 2

Alternative Diclofenac Fill Formulation

A lipophilic vehicle-based dual controlled-release matrix system was prepared containing the following ingredients.

| Name of the ingredient | % wt. |
| --- | --- |
| MCT | 58.5 |
| Glyceryl behanate | 0 |
| HPMC K4M | 15 |
| HPMC K15M | 1.25 |
| Aerosil 200 | 0.25 |
| Diclofenac sodium | 25 |

In vitro drug release studies were conducted using a USP dissolution apparatus II (paddles) at 50 rpm. The results are shown in FIG. 1. Experiments were conducted in dissolution media at a temperature of 37.0±0.5° C., for 8 hours in 6.8 phosphate buffer. Samples were periodically withdrawn and analyzed for Diclofenac sodium content using the ultraviolet ("UV") method. The samples were analyzed at a wavelength of 276 nm.

Example 3

Alternative Diclofenac Fill Formulation

A lipophilic vehicle-based dual controlled-release matrix system was prepared containing the following ingredients.

| Name of the ingredient | % wt. |
| --- | --- |
| MCT | 58 |
| Bees wax | 10 |
| HPMC K4M | 5.75 |
| HPMC K15M | 1.25 |
| Aerosil 200 | 0 |
| Diclofenac sodium | 25 |

Example 4

Preparation of a Diltiazem Hydrochloride Fill Formulation

A lipophilic vehicle-based dual controlled-release matrix system was prepared containing the following ingredients.

| Name of the ingredient | % wt of the matrix |
| --- | --- |
| MCT | 68.8 |
| Glyceryl behanate | 2.5 |
| HPMC K4M | 2.5 |
| HPMC K15M | 1 |
| HPMCK100M | 1 |
| Aerosil 200 | 0.2 |
| Diltiazem HCl | 24 |

Figure 2:
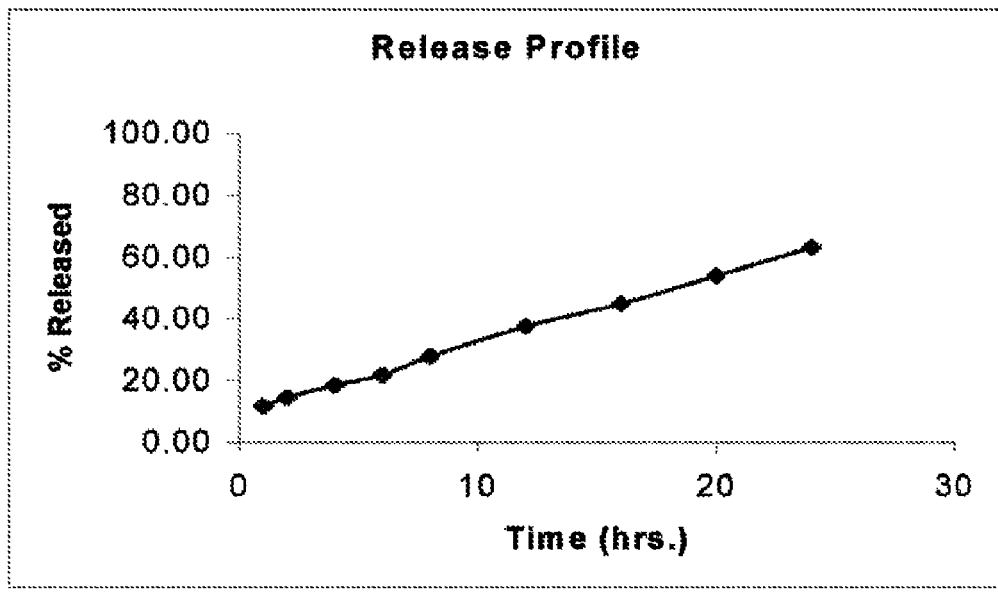
FIG. 2 shows the release profile of Diltiazem hydrochloride (% Diltiazem hydrochloride) versus time (hours) from a lipophilic vehicle-based matrix.

In vitro drug release studies were conducted using a USP dissolution apparatus II (paddles) at 100 rpm. The results are shown in FIG. 2. Experiments were conducted in dissolution media at a temperature of 37.0±0.5° C., for 24 hours in 6.5 phosphate buffer. Samples were periodically withdrawn and analyzed for diltiazem sodium content using the ultraviolet ("UV") method. The samples were analyzed at a wavelength of 236 nm. The release profile for diltiazem hydrochloride is shown in FIG. 2.

Example 5

Preparation of an Ibuprofen Fill Formulation

A lipophilic vehicle-based dual controlled-release matrix system was prepared containing the following ingredients.

| Name of the Ingredient | % wt. of fill matrix |
| --- | --- |
| MCT (medium chain triglyceride) | 41 |
| Hypromellose | 1 |
| Ibuprofen | 58 |

Figure 3:
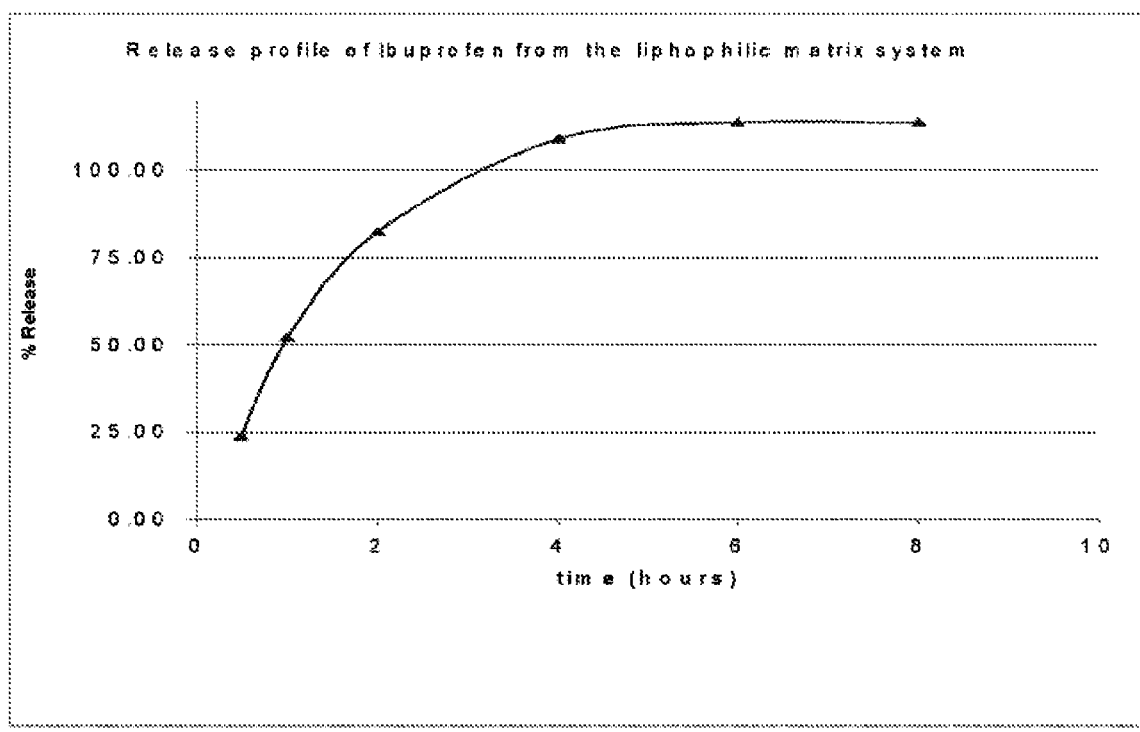
FIG. 3 shows the release profile of Ibuprofen (% ibuprofen) versus time (hours) from a lipophilic vehicle-based matrix.
Figure 4:
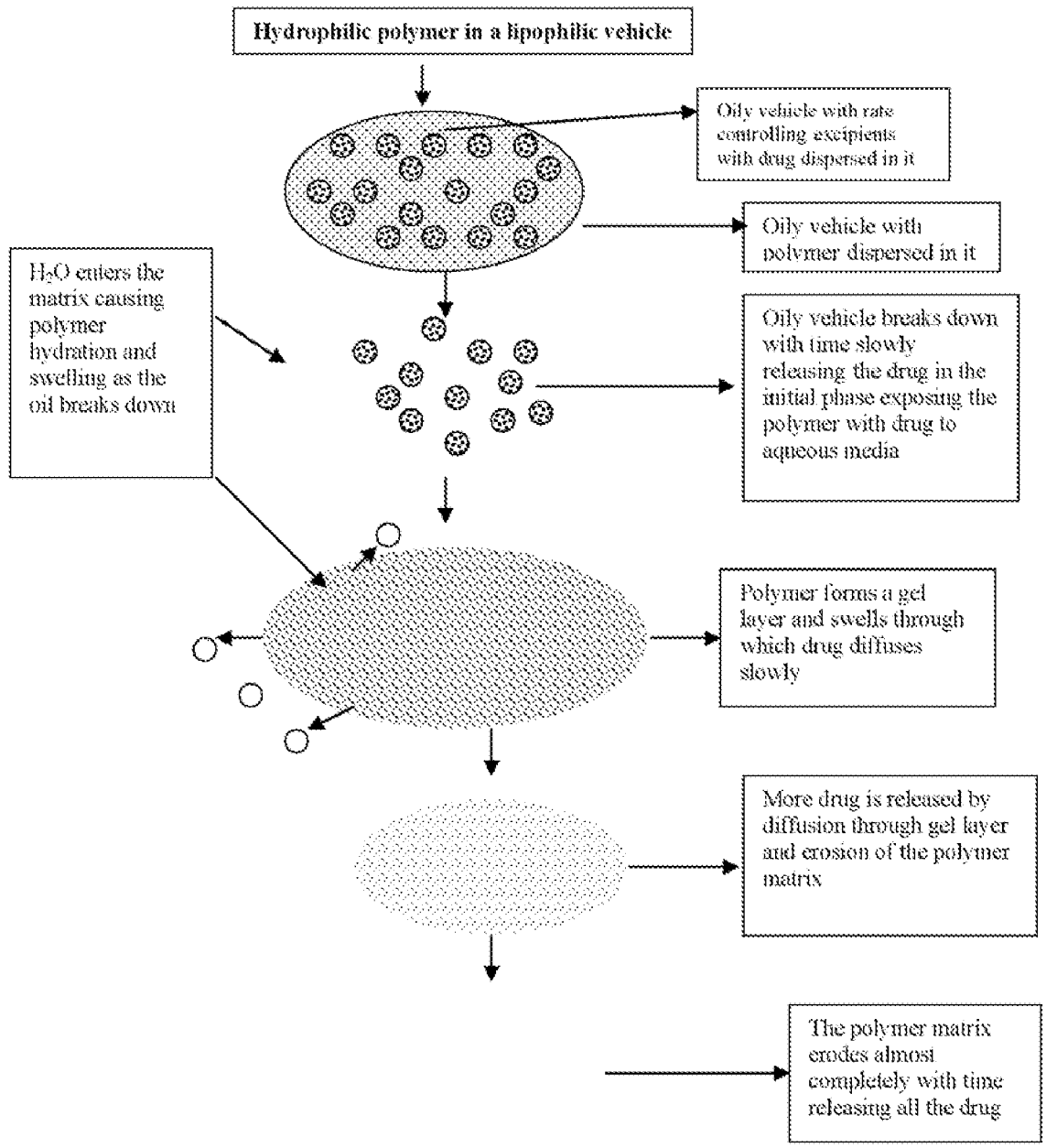
FIG. 4 is a schematic showing the mechanism of drug release from a lipophilic vehicle-based matrix.

In vitro drug release studies were conducted using a USP dissolution apparatus II (paddles) at 100 rpm. The results are shown in FIG. 3. Experiments were conducted in dissolution media at a temperature of 37.0±0.5° C., for 8 hours in 7.2 phosphate buffer. Samples were periodically withdrawn and analyzed for ibuprofen content using the ultraviolet ("UV") method. The samples were analyzed at a wavelength of 276 nm. The release profile for ibuprofen is shown in FIG. 3.

Example 6

Preparation of an Acetaminophen Fill Formulation

A lipophilic vehicle-based dual controlled-release matrix system was prepared containing the following ingredients.

| Name of the ingredient | % wt. of fill matrix |
| --- | --- |
| MCT(medium chain triglyceride) | 47.7 |
| Glyceryl behanate | 0.76 |
| Hypromellose | 1.5 |
| Acetaminophen | 50 |

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

I claim:

1. A soft capsule comprising a dual controlled release liquid lipophilic matrix, the matrix consisting essentially of:
   (a) a primary rate controlling barrier comprising a lipophilic oily vehicle;
   (b) a secondary rate controlling barrier comprising a hydrogel-forming polymeric material dispersed in the primary rate controlling barrier; and
   (c) a therapeutic, prophylactic or diagnostic agent entrapped within the primary and secondary rate controlling barriers,
   wherein upon contact with an aqueous medium, the hydrogel-forming polymeric material forms a hydrogel suspended in the lipophilic matrix, and
   wherein the release of the therapeutic, prophylactic, or diagnostic agent is biphasic.

2. The capsule of claim 1, wherein the lipophilic oily vehicle is selected from the group consisting of vegetable oils, medium chain mono-, di-, and triglycerides, mineral oil, glyceryl stearates, polyoxyethylated oleic glycerides, glyceryl monooleate, glyceryl monocaprate, glycercyl monocaprylate, propylene glycol monocaprylate, propylene glycol monolaurate, dimethylpolysiloxanes and combinations thereof.

3. The capsule of claim 1, wherein the lipophilic oily vehicle is present in an amount from about 3 to about 80% by weight of the matrix.

4. The capsule of claim 1, wherein the lipophilic oily vehicle is present in an amount from about 15 to about 75% by weight of the matrix.

5. The capsule of claim 1, wherein the primary rate controlling barrier further comprises one or more rate controlling excipients.

6. The capsule of claim 5, wherein the rate controlling excipients are selected from the group consisting of glyceryl behenate, gelucire, cremophor, hydrogenated vegetable oil, bees wax, and combinations thereof.

7. The capsule of claim 5, wherein the rate controlling excipients are present in amount from about 1% to about 50% by weight of the matrix.

8. The capsule of claim 7, wherein the rate controlling excipients are present in amount from about 5% to about 30% by weight of the matrix.

9. The capsule of claim 1, wherein the primary rate controlling barrier comprises one or more surfactants.

10. The capsule of claim 9, wherein the one or more surfactants is selected from the group consisting of polysorbates, sorbitan monoesters, ethoxylated castor oil, caprylocaproyl macrogol-8, glyceryl palmitostearate, glyceryl monooleate/stearate, and combinations thereof.

11. The capsule of claim 9, wherein the one or more surfactants are present in an amount from about 1 to 15% by weight of the matrix.

12. The capsule of claim 1, wherein the hydrogel-forming material is selected from the group consisting of cellulose ethers, cross-linked acrylates, alginates, xanthum gum, guar, carrageenan, high molecular weight polyvinyl pyrrolidone and mixtures thereof.

13. The capsule of claim 12, wherein the cellulose ether is hypromellose.

14. The capsule of claim 1, wherein the hydrogel-forming material is present in an amount from about 1 to about 80% by weight of the matrix.

15. The capsule of claim 14, wherein the hydrogel-forming material is present in amount from about 1 to about 50% by weight of the matrix.

16. The capsule of claim 1, wherein the therapeutic, prophylactic or diagnostic agent is dispersed or suspended, in part, in the primary rate controlling barrier.

17. The capsule of claim 1, wherein the therapeutic agent is selected from the group consisting of analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; anti-infective agents; anti-inflammatory agents; antimigraine agents; antineoplastic agents; antiparkinson drugs; antipruritic agents; antipsychotic agents; antipyretic agents; antispasmodic agents; antitubercular agents; antiulcer agents; antiviral agents; anxiolytic agents; appetite suppressants; attention deficit disorder and attention deficit hyperactivity disorder drugs; cardiovascular agents including calcium channel blockers, antianginal agents, central nervous system agents, beta-blockers and antiarrhythmic agents; central nervous system stimulants; diuretics; genetic materials;

hormonolytics; hypnotics; hypoglycemic agents; immunosuppressive agents; muscle relaxants; narcotic antagonists; nicotine; nutritional agents; parasympatholytics; peptide drugs; psychostimulants; sedatives; sialagogues, steroids; smoking cessation agents; sympathomimetics; tranquilizers; vasodilators; beta-agonist; tocolytic agents, and combinations thereof.

18. The capsule of claim 1, wherein the therapeutic agent is a drug that is prone to abuse.

19. The capsule of claim 1, wherein the release of the therapeutic, prophylactic, or diagnostic agent is modulated for up to 24 hours.

* * * * *